(12) United States Patent
Wack

(10) Patent No.: US 9,364,353 B2
(45) Date of Patent: Jun. 14, 2016

(54) BEND-CAPABLE STENT PROSTHESIS

(71) Applicant: C. R. Bard, Inc., Murray Hill, NJ (US)

(72) Inventor: Thilo Wack, Durmersheim (DE)

(73) Assignee: C.R. Bard, Inc., Murray Hill, NJ (US)

( * ) Notice: Subject to any disclaimer, the term of this patent is extended or adjusted under 35 U.S.C. 154(b) by 169 days.

(21) Appl. No.: 14/069,923

(22) Filed: Nov. 1, 2013

(65) Prior Publication Data

US 2014/0067045 A1 Mar. 6, 2014

Related U.S. Application Data

(63) Continuation of application No. 12/301,019, filed as application No. PCT/EP2007/054822 on May 18, 2007, now Pat. No. 8,574,286.

(30) Foreign Application Priority Data

May 18, 2006 (GB) .................................. 0609911.3

(51) Int. Cl.
*A61F 2/86* (2013.01)
*A61F 2/89* (2013.01)
(Continued)

(52) U.S. Cl.
CPC ... *A61F 2/89* (2013.01); *A61F 2/91* (2013.01); *A61F 2/915* (2013.01); *A61F 2002/91516* (2013.01); *A61F 2002/91525* (2013.01); *A61F 2002/91541* (2013.01); *A61F 2002/91558* (2013.01); *A61F 2230/0054* (2013.01)

(58) Field of Classification Search
CPC ............... A61F 2/82; A61F 2/86; A61F 2/89; A61F 2/91; A61F 2/915; A61F 2002/823; A61F 2002/825; A61F 2002/91533; A61F 2002/9155; A61F 2002/91558
See application file for complete search history.

(56) References Cited

U.S. PATENT DOCUMENTS 5,091,205 A 2/1992 Fan
5,464,419 A 11/1995 Glastra
(Continued)

FOREIGN PATENT DOCUMENTS

DE 04130431 A1 3/1993
DE 29621207 U1 1/1997
(Continued)

OTHER PUBLICATIONS

U.S. Appl. No. 10/362,040, filed Jun. 27, 2003 Office Action dated Aug. 2, 2006.
(Continued)

*Primary Examiner* — Ryan J Severson
(74) *Attorney, Agent, or Firm* — C.R. Bard Intellectual Property; Buchalter Nemer

(57) ABSTRACT

A stent is described, which includes a plurality of stenting rings, each stenting ring including a plurality of struts and points of inflection, each point of inflection connecting adjacent struts, the points of inflection of adjacent stenting rings facing each other along an axis parallel to a longitudinal axis of the stent in a radially expanded stenting disposition while the stent is in an unbent configuration. Adjacent stenting rings are connected by connectors extending from a point of inflection on one stenting ring to a facing point of inflection on another stenting ring, the connectors being linear along an entire length thereof and parallel to the longitudinal axis of the stent, each of the connectors having a length shorter than a length of each of the struts.

14 Claims, 4 Drawing Sheets

(51) Int. Cl.
*A61F 2/91* (2013.01)
*A61F 2/915* (2013.01)

(56) References Cited

U.S. PATENT DOCUMENTS

| | | |
|---|---|---|
| 5,527,353 A | 6/1996 | Schmitt |
| 5,591,223 A | 1/1997 | Lock et al. |
| 5,645,532 A | 7/1997 | Horgan |
| 5,725,572 A | 3/1998 | Lam et al. |
| 5,741,327 A | 4/1998 | Frantzen |
| 5,759,192 A | 6/1998 | Saunders |
| 5,800,511 A | 9/1998 | Mayer |
| 5,824,042 A | 10/1998 | Lombardi et al. |
| 5,824,059 A | 10/1998 | Wijay |
| 5,824,077 A | 10/1998 | Mayer |
| 5,843,118 A | 12/1998 | Sepetka et al. |
| 5,858,556 A | 1/1999 | Eckert et al. |
| 5,861,027 A | 1/1999 | Trapp |
| 5,868,783 A | 2/1999 | Tower |
| 5,922,020 A | 7/1999 | Klein et al. |
| 6,022,374 A | 2/2000 | Imran |
| 6,053,940 A | 4/2000 | Wijay |
| 6,056,187 A | 5/2000 | Acciai et al. |
| 6,086,611 A | 7/2000 | Duffy et al. |
| 6,099,561 A | 8/2000 | Alt |
| 6,174,329 B1 | 1/2001 | Callol et al. |
| 6,241,762 B1 | 6/2001 | Shanley |
| 6,270,524 B1 | 8/2001 | Kim |
| 6,293,966 B1 | 9/2001 | Frantzen |
| 6,312,456 B1 | 11/2001 | Kranz et al. |
| 6,334,871 B1 | 1/2002 | Dor et al. |
| 6,355,057 B1 | 3/2002 | DeMarais et al. |
| 6,379,381 B1 | 4/2002 | Hossainy et al. |
| 6,387,123 B1 | 5/2002 | Jacobs et al. |
| 6,409,752 B1 | 6/2002 | Boatman et al. |
| 6,451,047 B2 | 9/2002 | McCrea et al. |
| 6,471,721 B1 | 10/2002 | Dang |
| 6,475,233 B2 | 11/2002 | Trozera |
| 6,478,816 B1 | 11/2002 | Kveen et al. |
| 6,540,777 B2 | 4/2003 | Stenzel |
| 6,547,818 B1 | 4/2003 | Rourke et al. |
| 6,562,065 B1 | 5/2003 | Shanley |
| 6,585,757 B1 | 7/2003 | Callol |
| 6,605,110 B2 | 8/2003 | Harrison |
| 6,629,994 B2 | 10/2003 | Gomez et al. |
| 6,676,700 B1 | 1/2004 | Jacobs et al. |
| 6,770,089 B1 | 8/2004 | Hong et al. |
| 6,797,217 B2 | 9/2004 | McCrea et al. |
| 6,827,734 B2 | 12/2004 | Fariabi |
| 6,878,162 B2 | 4/2005 | Bales et al. |
| 6,979,346 B1 | 12/2005 | Hossainy et al. |
| 7,060,093 B2 | 6/2006 | Dang et al. |
| 7,135,038 B1 | 11/2006 | Limon |
| 7,175,654 B2 | 2/2007 | Bonsignore et al. |
| 7,462,190 B2 | 12/2008 | Lombardi |
| 7,468,071 B2 | 12/2008 | Edwin et al. |
| 7,479,157 B2 | 1/2009 | Weber et al. |
| 7,691,461 B1 | 4/2010 | Prabhu |
| 7,771,463 B2 | 8/2010 | Ton et al. |
| 7,772,659 B2 | 8/2010 | Rodmacq et al. |
| 8,043,364 B2 | 10/2011 | Lombardi et al. |
| 8,152,842 B2 | 4/2012 | Schlun |
| 8,292,950 B2 | 10/2012 | Dorn et al. |
| 8,322,593 B2 | 12/2012 | Wack |
| 8,403,978 B2 | 3/2013 | Schlun et al. |
| 8,475,520 B2 | 7/2013 | Wack et al. |
| 8,500,793 B2 | 8/2013 | Zipse et al. |
| 8,518,101 B2 | 8/2013 | Dreher |
| 8,551,156 B2 | 10/2013 | Wack et al. |
| 8,574,286 B2 | 11/2013 | Wack |
| 2002/0007212 A1 | 1/2002 | Brown et al. |
| 2002/0116044 A1 | 8/2002 | Cottone et al. |
| 2002/0116051 A1 | 8/2002 | Cragg |
| 2002/0138136 A1 | 9/2002 | Chandresekaran et al. |
| 2002/0193867 A1 | 12/2002 | Gladdish et al. |
| 2002/0193869 A1 | 12/2002 | Dang |
| 2002/0198589 A1 | 12/2002 | Leong |
| 2003/0055485 A1 | 3/2003 | Lee et al. |
| 2003/0135254 A1 | 7/2003 | Curcio et al. |
| 2003/0144725 A1 | 7/2003 | Lombardi |
| 2003/0216807 A1 | 11/2003 | Jones et al. |
| 2003/0225448 A1 | 12/2003 | Gerberding |
| 2004/0015228 A1 | 1/2004 | Lombardi et al. |
| 2004/0015229 A1 | 1/2004 | Fulkerson et al. |
| 2004/0034402 A1 | 2/2004 | Bales et al. |
| 2004/0044401 A1 | 3/2004 | Bales et al. |
| 2004/0073290 A1 | 4/2004 | Chouinard |
| 2004/0073291 A1 | 4/2004 | Brown et al. |
| 2004/0117002 A1 | 6/2004 | Girton et al. |
| 2004/0230293 A1 | 11/2004 | Yip et al. |
| 2004/0236400 A1 | 11/2004 | Edwin et al. |
| 2004/0236409 A1 | 11/2004 | Pelton et al. |
| 2004/0254637 A1 | 12/2004 | Yang et al. |
| 2005/0049682 A1 | 3/2005 | Leanna et al. |
| 2005/0060025 A1 | 3/2005 | Mackiewicz et al. |
| 2005/0149168 A1 | 7/2005 | Gregorich |
| 2005/0172471 A1 | 8/2005 | Vietmeier |
| 2005/0182477 A1 | 8/2005 | White |
| 2005/0222667 A1 | 10/2005 | Hunt |
| 2005/0278019 A1 | 12/2005 | Gregorich |
| 2006/0030934 A1 | 2/2006 | Hogendijk et al. |
| 2006/0064153 A1 | 3/2006 | Langhans et al. |
| 2006/0216431 A1 | 9/2006 | Kerrigan |
| 2006/0241741 A1 | 10/2006 | Lootz |
| 2006/0265049 A1 | 11/2006 | Gray et al. |
| 2007/0112421 A1 | 5/2007 | O'Brien |
| 2007/0219624 A1 | 9/2007 | Brown et al. |
| 2008/0051885 A1 | 2/2008 | Llanos et al. |
| 2008/0188924 A1 | 8/2008 | Prabhu |
| 2009/0125092 A1 | 5/2009 | McCrea et al. |
| 2009/0125099 A1 | 5/2009 | Weber et al. |
| 2009/0200360 A1 | 8/2009 | Wack |
| 2009/0204203 A1 | 8/2009 | Allen et al. |
| 2009/0264982 A1 | 10/2009 | Krause et al. |
| 2010/0016949 A1 | 1/2010 | Wack |
| 2010/0070021 A1 | 3/2010 | Wack et al. |
| 2010/0114298 A1 | 5/2010 | Dorn et al. |
| 2010/0191321 A1 | 7/2010 | Schlun et al. |
| 2010/0204784 A1 | 8/2010 | Molaei et al. |
| 2010/0211161 A1 | 8/2010 | Dreher |
| 2010/0234936 A1 | 9/2010 | Schlun |
| 2010/0249903 A1 | 9/2010 | Wack et al. |
| 2010/0298921 A1 | 11/2010 | Schlun et al. |
| 2011/0196473 A1 | 8/2011 | McCrea et al. |
| 2011/0198327 A1 | 8/2011 | Prabhu |
| 2011/0245905 A1 | 10/2011 | Weber et al. |
| 2011/0319977 A1 | 12/2011 | Pandelidis et al. |
| 2012/0041542 A1 | 2/2012 | Lombardi et al. |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |
| EP | 1157673 A2 | 11/2001 |
| EP | 1190685 A2 | 3/2002 |
| EP | 1212991 A2 | 6/2002 |
| EP | 1245203 A2 | 10/2002 |
| EP | 1255507 A1 | 11/2002 |
| EP | 1356789 A1 | 10/2003 |
| EP | 1433438 A2 | 6/2004 |
| EP | 1488763 A2 | 12/2004 |
| EP | 1767240 A1 | 3/2007 |
| EP | 2134301 A2 | 12/2009 |
| FR | 2626046 A1 | 7/1989 |

(56) References Cited

FOREIGN PATENT DOCUMENTS

| | | | |
|---|---|---|---|
| GB | 453944 A | 9/1936 |
| JP | 07315147 A | 12/1995 |
| JP | 2004-506477 A | 3/2004 |
| JP | 2007-504891 A | 3/2007 |
| JP | 4827965 B2 | 11/2011 |
| JP | 4933018 B2 | 5/2012 |
| WO | 9417754 A1 | 8/1994 |
| WO | 9503010 A1 | 2/1995 |
| WO | 9626689 A1 | 9/1996 |
| WO | 9733534 A1 | 9/1997 |
| WO | 9820810 A1 | 5/1998 |
| WO | 9915108 A2 | 4/1999 |
| WO | 9938457 A1 | 8/1999 |
| WO | 9949928 A1 | 10/1999 |
| WO | 9955253 A1 | 11/1999 |
| WO | 0045742 A1 | 8/2000 |
| WO | 0049971 A1 | 8/2000 |
| WO | 0064375 A1 | 11/2000 |
| WO | 0101889 A1 | 1/2001 |
| WO | 0132102 A1 | 5/2001 |
| WO | 0158384 A1 | 8/2001 |
| WO | 0176508 A2 | 10/2001 |
| WO | 0215820 A2 | 2/2002 |
| WO | 0249544 A1 | 6/2002 |
| WO | 03055414 A1 | 7/2003 |
| WO | 03075797 | 9/2003 |
| WO | 03101343 A1 | 12/2003 |
| WO | 2004019820 A1 | 3/2004 |
| WO | 2004028408 A1 | 4/2004 |
| WO | 2004032802 A2 | 4/2004 |
| WO | 2004058384 A1 | 7/2004 |
| WO | 2005067816 A1 | 7/2005 |
| WO | 2005072652 A1 | 8/2005 |
| WO | 2005104991 A1 | 11/2005 |
| WO | 2005032403 A3 | 12/2005 |
| WO | 2006010636 A1 | 2/2006 |
| WO | 2006010638 A1 | 2/2006 |
| WO | 2006014768 A1 | 2/2006 |
| WO | 2006025847 A2 | 3/2006 |
| WO | 2006036912 A2 | 4/2006 |
| WO | 2006047977 A1 | 5/2006 |
| WO | 2006064153 A1 | 6/2006 |
| WO | 2007073413 A1 | 6/2007 |
| WO | 2006026778 A3 | 11/2007 |
| WO | 2007131798 A1 | 11/2007 |
| WO | 2007135090 A1 | 11/2007 |
| WO | 2008006830 A1 | 1/2008 |
| WO | 2008022949 A1 | 2/2008 |
| WO | 2008022950 A1 | 2/2008 |
| WO | 2008025762 A1 | 3/2008 |
| WO | 2008028964 A2 | 3/2008 |
| WO | 2008055980 A1 | 5/2008 |
| WO | 2008068279 A1 | 6/2008 |
| WO | 2008101987 A1 | 8/2008 |
| WO | 2008119837 A2 | 10/2008 |
| WO | 2009030748 A2 | 3/2009 |

OTHER PUBLICATIONS

U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Examiner's Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/440,415, filed Mar. 6, 2009 Notice of Allowance dated Apr. 3, 2013.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.
U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.

(56) References Cited

OTHER PUBLICATIONS

U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12. 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 12/594,531, filed Oct. 2, 2009 Non-Final Office Action dated Oct. 2, 2012.
U.S. Appl. No. 12/676,584, filed Mar. 4, 2010 Non-Final Office Action dated May 24, 2013.
U.S. Appl. No. 13/279,189, filed Oct. 21, 2011 Final Office Action dated May 2, 2013.
U.S. Appl. No. 13/279,189, filed Oct. 21, 2011 Non-Final Office Action dated Oct. 17, 2012.

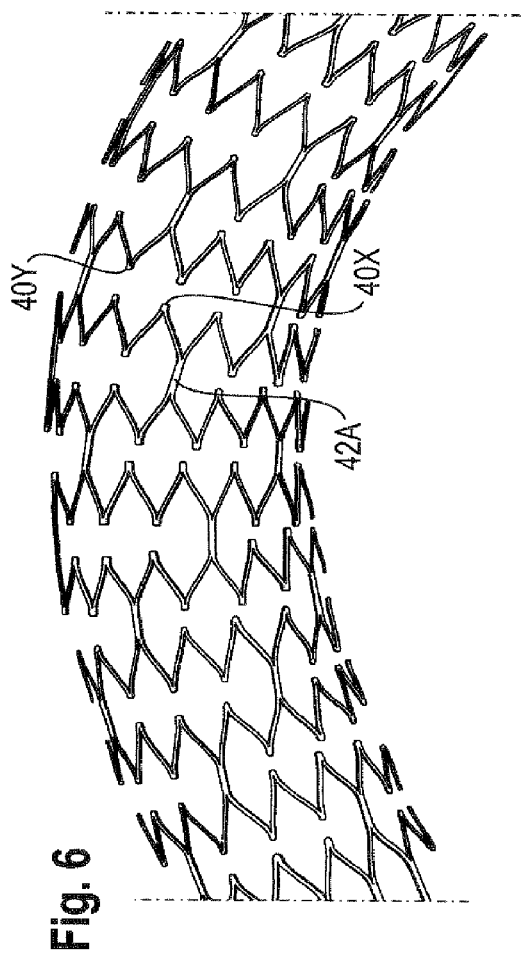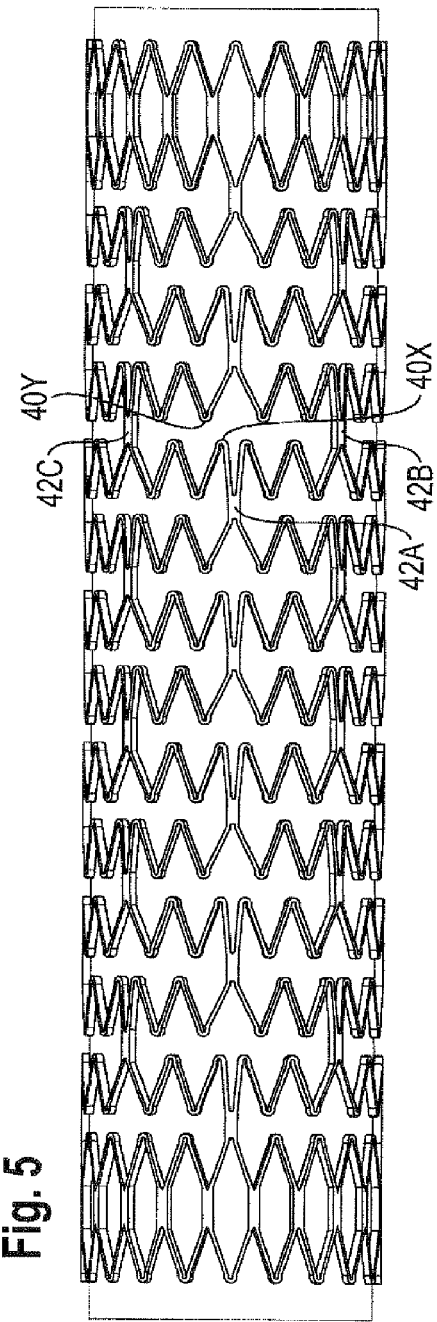

BEND-CAPABLE STENT PROSTHESIS

PRIORITY

This application is a continuation of U.S. patent application Ser. No. 12/301,019, filed Feb. 2, 2009, now U.S. Pat. No. 8,574,286, which was filed as a U.S. national stage application under 35 USC §371 of International Application No. PCT/EP2007/054822, filed May 18, 2007, claiming priority to United Kingdom Patent Application No. 0609911.3, filed May 18, 2006, each of which is incorporated by reference in its entirety into this application.

FIELD OF THE INVENTION

This invention relates to a stent prosthesis which is tubular and has a matrix of struts that provide a stenting action that holds bodily tissue radially away from any lumen defined by the stent matrix, around a longitudinal axis of the prosthesis. One such prosthesis is disclosed in applicant's WO 01/32102.

BACKGROUND

Currently, the great majority of stents delivered transluminally and percutaneously to a stenting site in a human body are made of a biologically compatible material which is a metal. Many stents are made of stainless steel, and many others are made of nickel titanium shape memory alloy. The nickel titanium stents are invariably self-expanding stents that utilise a shape memory effect for moving between a radially compact transluminal delivery disposition and a radially larger stenting disposition after placement in the body. Stainless steel stents are often delivered on a balloon catheter, with inflation of the balloon causing plastic deformation of the material of the struts, but other stainless steel stents rely on the resilience of the steel to spring open when a surrounding sheath is retracted relative to the stent being deployed.

However, in all cases, it is difficult to endow the stent strut matrix with a degree of flexibility that comes anywhere near the degree of flexibility of the natural bodily tissue at the stenting site. The strength and resilience of the stent matrix, that serves to push radially outwardly the bodily tissue at the stenting site, is difficult to reconcile with the flexibility in bending that the natural tissue and the stent is capable of exhibiting, in normal life of the patient carrying the stent. It is one object of the present invention to improve the performance of a stent prosthesis in bending, after it has been deployed in the body of a patient.

To explain the problem, reference will now be made to applicant's WO 01/32102, specifically drawing FIGS. 3 and 4, and the text, of WO 01/32102. Indeed, accompanying drawing FIGS. 1 and 2 are the same as FIGS. 3 and 4 of WO 01/32102.

Looking at accompanying FIG. 1, we see part of the circumference of a tubular workpiece of nickel titanium shape memory alloy, in side view. The tube has a diameter D and a multiplicity of slits 20, 22 and 24, through the wall thickness of the tubular workpiece, all parallel to each other and to the longitudinal axis of the workpiece and creating out of the original solid tubular workpiece a lattice which can be expanded radially outwardly, (for example on a mandrel) to the expanded configuration of drawing FIG. 2 (again in side view). Out of the multitude of parallel slits can now be recognised as a sequence of 10 stenting rings, all displaying a zig-zag advance around the circumference of the prosthesis. Terminal zig-zag rings 30 are composed of 24 struts 32 interspersed by points of inflection 34, giving the end view of the prosthesis the appearance of a crown with twelve points.

The eight zig-zag rings at intermediate points along the length of the stent, between the two end rings 30, are referenced 36. They are made up of struts 38 which are all much the same length, somewhat shorter than end struts 32. Between any two struts of any of the zig-zag stenting rings there is a point of inflection 40. In the two end rings 30, all twelve of these points of inflection remote from the crown end of the terminal ring 30 are connected to a corresponding point of inflection 40, head to head, in the next adjacent internal stenting ring 36. However, between any two internal stenting rings 36, not all the twelve points of inflection, found spaced around the circumference of the prosthesis, are joined to corresponding points of inflection on the next adjacent stenting ring 36. Indeed, reverting to FIG. 1, it is easy to see that there will be only four connector portions 42, linking any two adjacent internal stenting rings 36.

Thinking about advance of the prosthesis of FIG. 1, in its compact disposition, along a tortuous, transluminal, delivery path to the stenting site, as the stent bends around a sharp bend in the delivery path, on the inside of any such bend, for example at point 44 on FIG. 1, the points of inflection facing each other across the gap 60 will approach one another. Depending on the length of the diametrically opposed connector portions 42 connecting stenting rings 36B and 36C, the two unconnected points of inflection will come into contact with each other in the middle of the gap 60, in dependence upon how sharp is the bend that the stent is negotiating in the tortuous path at that time. The longer the axial gap between adjacent stenting rings, the greater the capability of the stent for negotiating ever tighter bends in the delivery path lumen.

But what of the performance of the stent in bending, after it has been deployed at the stenting site.

We can see from FIG. 2 that the pattern of connector portions 42 is symmetrical. That is to say, standing on one of these connector portions, and looking along the length of the prosthesis, the pattern of connectors to the left of the line of view is a mirror image of the pattern of connectors to the right of that line of view. If we switch to consideration of drawing FIG. 3, which shows a portion of the strut network of the stent of FIGS. 1 and 2, this is more readily evident. Just as points of inflection on the inside of a tight bend of the stent in its compact disposition of FIG. 1 can butt up against each other face to face, so can the same phenomenon occur when the expanded stent of FIG. 2 is subject to sharp bending. Any such intermittent abutment of otherwise free points of inflection is liable to have negative effects including, for example, irritation or injury to bodily tissue caught between the abutting points of inflection, or even incipient buckling of the stent with the potential to reduce flow of bodily fluid through the stent lumen to dangerously low levels.

It is one object of the present invention to mitigate these risks.

SUMMARY OF THE INVENTION

The matrix of struts of a radially expandable stent can be looked upon as a two dimensional lattice (when the tubular stent is opened out flat on a plane) and if the lattice has a regular structure (which it invariably does) then it is possible to define the lattice using a concept familiar in crystallography, namely, the "unit cell" characteristic of a space lattice of points, with each point of the space lattice corresponding to one of the connector portions in the stent matrix. Conventionally, as in the structure shown in FIGS. 1 to 3 discussed above, the unit cell is aligned with the longitudinal axis of the prosthesis. In accordance with one aspect of the present invention, however, the axially adjacent stenting rings are separated only by a small gap, and the unit cell is deliberately "skewed" with respect to the longitudinal axis of the prosthesis. This has the consequence that, when the expanded stent prosthesis is sharply bent, points of inflection that would otherwise approach each other head to head are prompted by the stresses arising in the lattice of struts to shear sideways, in opposite directions around the circumference of the stent prosthesis so that, when the tightness of the bend is finally such as to bring the points of inflection close to each other, they pass side by side rather than impact head to head.

Note that the axial gap between two radially expanded rings of a straight stent is virtually identical to the length of the gap between the same two rings in the compressed stent n the delivery catheter. But the points of inflection are much further away from the longitudinal axis, with the consequence that the amount of axial movement of facing points of inflection, for any particular degree of bending of the axis, is much greater with the stent radially expanded. A small axial gap might therefore suffice, in the delivery disposition of a stent while being inadequate to prevent head to head impact in the expanded disposition.

The small gap between axially adjacent stenting rings is important for the establishment of usefully high radially outwardly directed stenting forces. It is the tendency of the points of inflection (peaks) to pass by each other, when the stent bends, in overlapping side-by-side relationship, that opens up the possibility to keep the gap so small.

A relatively simple way to accomplish this desirable result is to arrange that, when the number of struts "N" of any stenting ring B lying between any two adjacent connector portions is such that N/2 is an even number, so that the connector portions at one axial end of ring B cannot lie circumferentially halfway between any two connector portions on the other axial end of ring B. Note that in FIG. 2 above, there are six struts of any particular stenting ring 36 between adjacent connector portions 42 on the same axial end of that stenting ring 36. Half of six is three, and three is not an even number. Proceeding from any particular connector portion 42 of the matrix of FIG. 2, it takes three struts to reach the next adjacent connector portion, whichever path one takes when departing from the base connector portion 42. In accordance with the present invention, the number of struts taken to reach the next adjacent connector portion 42 is not always the same. In consequence, the stresses imposed on the struts by bending the prosthesis sharply (into a banana shape) are going to be distributed asymmetrically with respect to any particular connecter portion 42 and it is this asymmetric stress distribution that will skew the free points of inflection relative to those facing them in the next adjacent stenting ring, so that they do not abut each other head to head on the inside of the bend of the banana shape.

Thus, in accordance with another aspect of the invention, there is provided a prosthesis that is expandable from a radially compact delivery disposition to a radially expanded stenting disposition, and is composed of a stack of zig-zag stenting rings of struts that end in points of inflection spaced around the circumference of a stenting lumen that is itself on a longitudinal axis of the stent, each of the points of inflection being located at one or the other of the two axial ends of each ring, with adjacent rings A, B, C in the stack being connected by straight connectors linking selected facing pairs of points of inflection of each two adjacent rings, circumferentially intervening pairs of facing points of inflection being unconnected, and with progress from strut to strut via the points of inflection, around the full circumference of one of the stenting rings B, namely one that is located axially between adjacent rings A and C in the stack, the connector ends encountered during such progress connect ring B alternately, first to ring A, then to ring C, then to ring A again, and so on characterised in that the connectors are parallel to the longitudinal axis and are shorter than said strut length the pairs of unconnected points of inflection remain facing, in the radially expanded disposition, for as long as the longitudinal axis remains a straight line the number of struts in ring B that lie between successive said connector ends that join ring B alternately to ring A, then ring C, is a whole number that alternates between two different values; and the connectors are so short that, when the stent functioning as a stent is caused to bend, such that the longitudinal axis becomes arcuate, the facing pairs of unconnected points of inflection that are on the inside of the bend eventually pass axially past each other, side by side, circumferentially spaced from each other, rather than impacting on each other, head to head.

A stent construction in accordance with the invention is only marginally more complex than the simple and "classic" zig-zag stenting ring construction evident from drawing FIGS. 1 to 3. The stenting rings can be a simple zig-zag construction of struts all the same length, and the connector portions can be nothing more than a plane of abutment between abutting points of inflection in adjacent zig-zag stenting rings, or simple, short, straight portions aligned with the longitudinal axis of the prosthesis. This is advantageous, when it comes to modelling the fatigue performance of the stent, something of significant importance for government regulatory authorities and for optimising stent performance long term.

There is another valuable performance enhancement that the present invention can deliver, namely attainment of full performance of any particular "theoretical" stent matrix. In reality, every placement of a stent is an individual unique event. To some extent, every stent of shape memory alloy has had its remembered shape set in a unique heat treatment step. Referring back, once again, to WO 01/32102, we set the remembered shape before removing bridges of "scrap" material between stenting rings. In consequence, remembered shapes are highly orderly and regular, much closer to the "theoretical" zig-zag shape than can be attained when the rings are only connected by a minimum of connectors during the shape-setting step. We can have this advantage also with stents in accordance with the present invention, to optimise the bending performance of the stents, and the fatigue resistance that comes from having stress distributions close to optimal, every time.

For a clear understanding of the invention definitions are useful for "strut length" and "connector length". Fortunately, such definitions are more or less self-evident, after consideration of how stents are made.

Normally, one begins with a tubular workpiece and creates in it a multitude of slits that extend through the wall thickness. They have their length direction more or less lengthwise along the tube. Circumferentially, adjacent slits are axially staggered. This is not unlike the way of making a simple "expanded metal" sheet having diamond-shaped apertures, familiar to structural engineers, and those who clad dangerous machinery in see-through metal sheet material to serve as safety guards.

For stent making, a useful extra step is to remove many of the residual links between adjacent diamonds. See again WO 01/32102, mentioned above.

The slit creation step can be by a chemical process such as etching or a physical process such as laser cutting. For nickel titanium shape memory alloys, the usual method is laser cutting.

So, now, how to define strut length and connector length? These lengths emerge quite simply from an inspection of the axial lengths by which circumferentially adjacent slits overlap. For a strut length one would measure axially from the end of one slit (that is defining one of the two flanks surfaces of the strut under consideration) to the end of the circumferentially next adjacent slit that has, as one of its defining long walls, the other flank surface of the strut whose length is to be ascertained. This method yields relatively short lengths. It is as if one were a tailor, and were to measure arm length from the armpit rather than from a point on top of the shoulder of the person being fitted.

The same logic applies when determining connector lengths. They correspond to the length of the gap that is created, when material is moved from the stent workpiece, in the unslitted material between two co-linear slits through the wall of the workpiece, said removal of material revealing two axially facing points of inflection when the stent matrix is subject to radial expansion. Thus, in the limiting case, the connector length is the same as the width of the laser beam that removed material to create that gap. Again, see WO 01/32102 mentioned above.

Of course, connector lengths and strut lengths can vary over the stent. Some of its stenting rings may have longer struts than others. However, except for very special cases, a stent is indifferent to rotation about is long axis, so that changes in the rotational orientation of the stent relative to the bodily lumen being stented, during advancement of the stent along the lumen to the stenting site, do not render the stent unfit for placement. Thus, for purposes of clarity in the here-claimed invention, it will always be possible to divine clearly a strut length and a connector length, for testing whether the definition of the invention is met in any particular zone of a stent that corresponds to two adjacent stenting rings and the gap in between.

With the published state of the art there are disclosures, such as in US2004/0117002 and US 2003/0225448, of stents composed of zig-zag stenting rings with straight connectors that join adjacent stenting rings peak-to-peak and with alternating whole numbers of struts lying between circumferentially adjacent connectors terminating in any one ring of such struts. Such stents exhibit face to face (otherwise here called "peak to peak") facing points of inflection in the radially compact pre-expanded disposition of the stent. Such stents are relatively easy to make by laser cutting of a precursor tube of raw material. Whether such stents still exhibit face to face points of inflection after expansion is unclear. What happens when the stents bend is also unclear. What is clear is that the writers of these prior publications did not include any teaching about how facing points of inflecting may tend to move in opposite circumferential directions on bending of the stent, and thereby ease away from head to head collision. A failure to recognise this phenomenon results in a failure to appreciate the scope to reduce the length of the connectors connecting adjacent stenting rings, thereby missing a chance to maximise radially stenting force and strut coverage of the wall of the bodily lumen that has been stented.

The disclosure of WO98/20810 is instructive. It describes laser cut stents of nickel titanium shape memory alloy, with zig-zag stenting rings that expand to a stenting diameter. It teaches that the straight connectors linking axially adjacent stenting rings are to be at a slant to the longitudinal axis so that what would otherwise be the facing points of the "V-shaped segments" are circumferentially staggered, to minimise contact between these peaks when the expanded stent is bent such that the longitudinal axis becomes arcuate. Another reason for staggering the V-points around the circumferences is to improve the homogeneity of coverage of the lumen wall with the strut matrix of the stent, to leave no zones of coverage of the lumen wall tissue that are more sparse than other zones. The connectors shown in the drawings do appear to be quite long and it is of course self-evident that, the longer the connectors, the longer are the gaps between axially adjacent zig-zag rings, such gaps corresponding to sparse coverage of the lumen wall bodily tissue in the zones of tissue in the gaps between the rings. In other words, the shorter the connectors, the less need there is to stagger the V-point peaks circumferentially, in order to maintain lumen wall coverage by the matrix of struts of the stent.

When assimilating the disclosure value of WO98/20810 it is instructive to imagine the stent in radially fully expanded disposition. The circumferential arc between two points of inflection is multiple times more than in the radially compressed delivery, and multiple times more than the circumferential distance between the opposite ends of a slanting connector. This has the consequence that the degree by which peak to peak impact is alleviated, by a short slanting connector, is disappointingly small, and gets relatively smaller with every increase in diameter of the expanded stent. By contrast, with the present invention, the greater the diameter of the expanded stent, the more powerful the effect to circumferentially stagger the points of inflection.

It will be evident to the skilled reader that the term "stenting ring" can be understood also to include in its scope successive turns around a stent lumen of a spiral that is composed of struts in a zig-zag arrangement which spiral advances along the stent lumen away form one of the stent and towards the other.

Struts need not be of constant cross-section. Indeed, for optimisation of stress distribution within the struts, and hence of the fatigue performance of the stent the cross-section will indeed change, along the length of each strut. The struts need not all be the same as each other. There could be different strut species, either from ring to ring or, indeed, within a stenting ring. A common arrangement is to have rings of longer struts at each end of the stent, the shorter struts at a mid-length portion, providing greater radially outward stenting force.

The stent can be a bare stent or a covered stent such as a stent graft. The stent may be a drug-eluting stent. The stent may have a function other than to hold a bodily lumen open against stenosis. For example, the stent could be part of a filter device for temporary placement in a bodily lumen, or an anchor for some other device that is to perform a therapeutic function within a bodily lumen.

BRIEF DESCRIPTION OF THE DRAWINGS

For a better understanding of the present invention, and to show more clearly how the same may be carried into effect, reference will now be made, by way of example, to the accompanying drawings, in which:

FIG. 5 is a photographic side view of a stent prosthesis which exhibits the strut and connector matrix of FIG. 4, expanded but not subject to any bending stresses; and FIG. 6 is a photographic side view of part of the stent prosthesis of FIG. 5, but bent into a "banana" shape to reveal how the points of inflection move relative to each other and relative to the addressed unbent configuration of FIG. 5.

DETAILED DESCRIPTION

Figure 1:
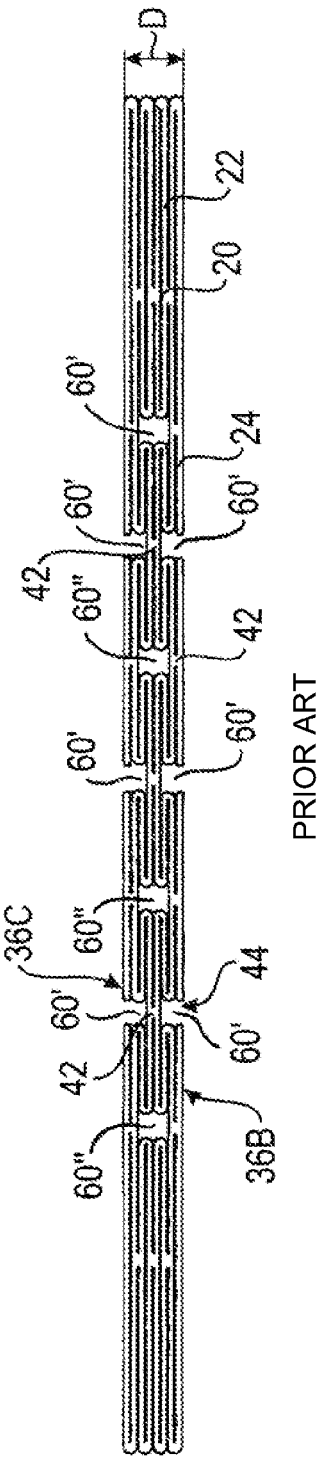
FIGS. 1 and 2 are side views of the stent described in WO 01/32102, with FIG. 1 in the compact delivery disposition and FIG. 2 in the radially expanded deployed disposition of the prosthesis.
Figure 2:
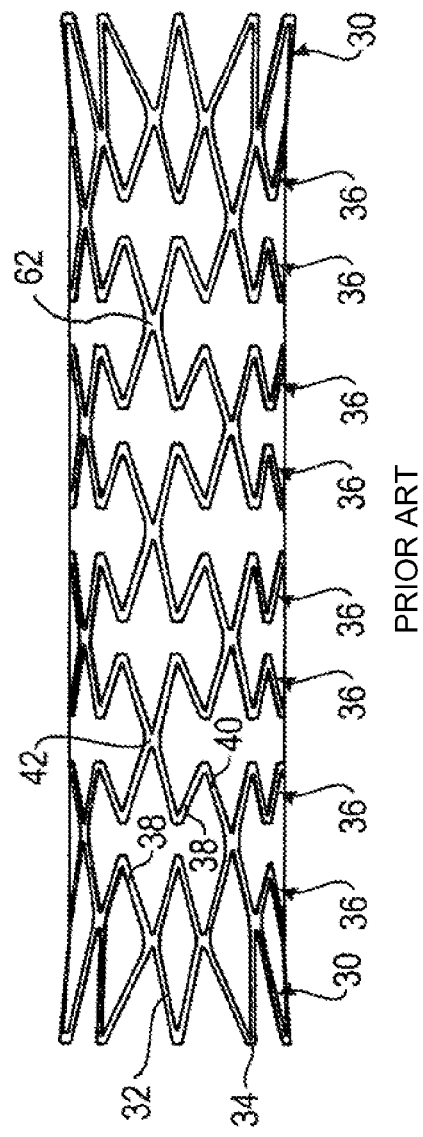

What is shown in FIGS. 1, 2 has been described above and in applicant's earlier WO 01/32102. The reader is referred to the passages above and to the prior publication.

Figure 3:
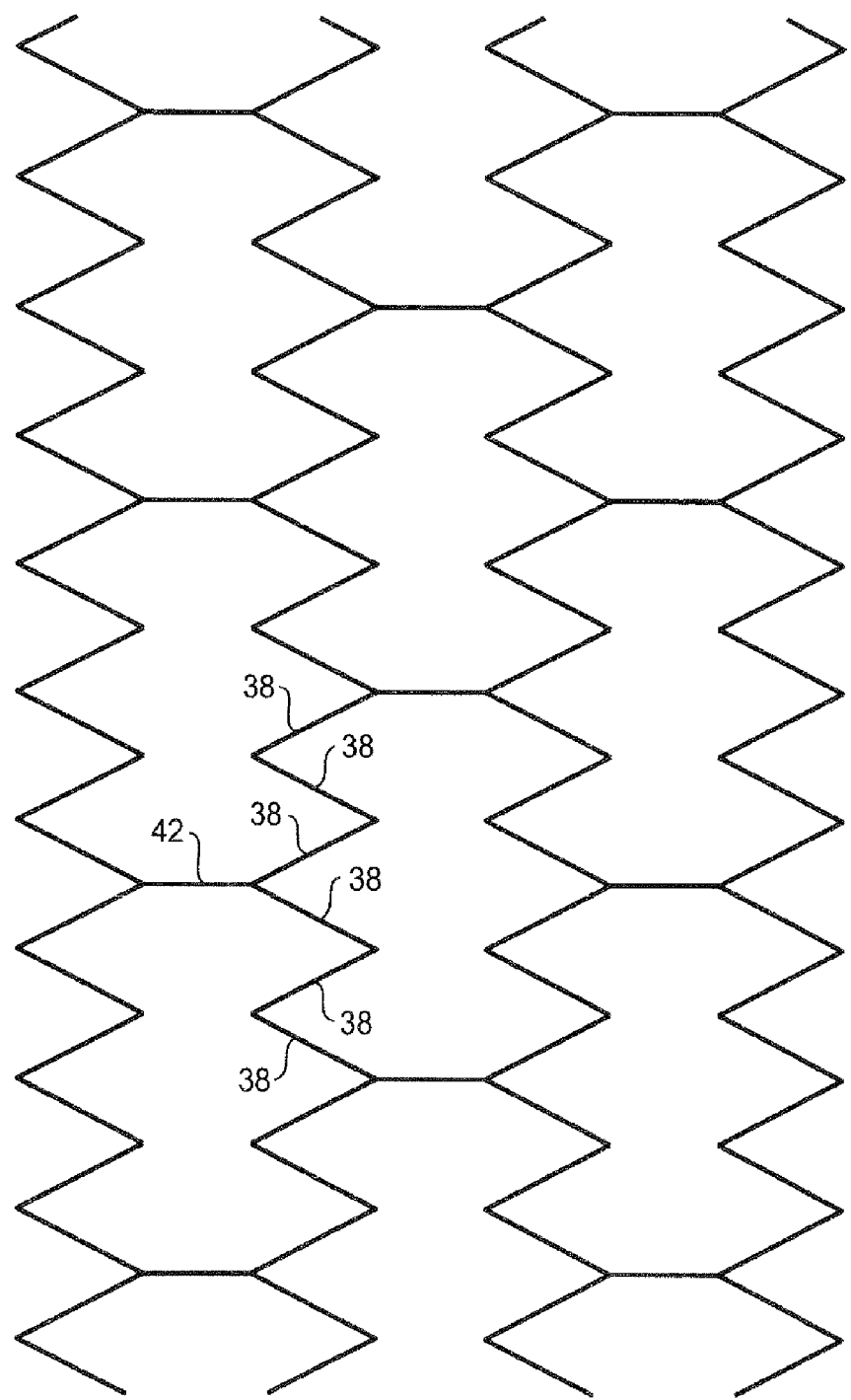
FIG. 3 is a diagram of symmetrical matrix of connector portions (not unlike the embodiment of FIGS. 1 and 2), opened out flat on a plane.

FIG. 3 is not unlike the embodiment of FIGS. 1 and 2, but the length of the elongate connectors 42 helps to reveal the pattern of connectors in the lattice.

Figure 4:
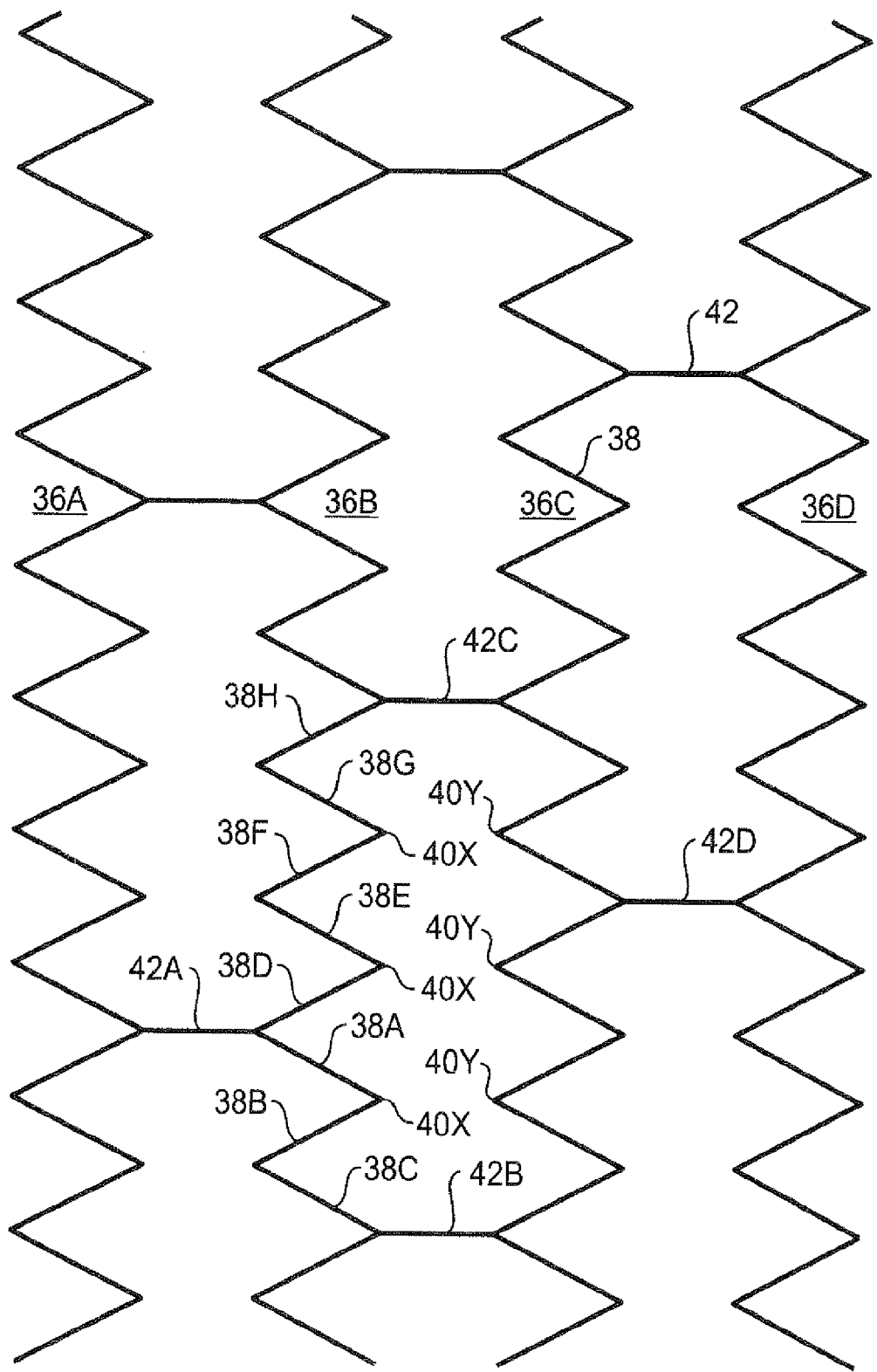
FIG. 4 is a diagram corresponding to that of FIG. 3, but with a matrix of struts and connectors in accordance with the present invention

FIG. 4 reveals a matrix of struts 38 and connectors 42 spacing apart a succession of zig-zag stenting rings 36 (four are visible in FIG. 4). Starting from connector 42A, we can reach adjacent connector 42B via a sequence of three struts 38ABC. But not all adjacent connectors are as close. Consider adjacent connector 42C. It takes five struts, namely struts 38D to H, to reach connector 42C. The pattern is repeated throughout the matrix. Note that the connector 42D that links zig-zag rings 36C and 36D is displaced circumferentially sideways from connector 42A, unlike the arrangement in FIG. 3. If we imagine in FIG. 4 connectors 42A and 42D lying on the inside of a severe bend of the expanded stent matrix, so that the points of inflection 40X on zig-zag ring 36B, and the points of inflection 40Y on zig-zag ring 36C, are moving towards each other, the stresses imposed by connector 42A on stenting ring 36B and those imposed on stenting ring 36C by connector 42D will be unsymmetrical. It does not require a great exercise of imagination to visualise points of inflection 40x and points of inflection 40Y failing to meet each other face to face when the bend is tight enough but, instead, sliding past each other, with spacing.

Turning to drawing FIGS. 5 and 6, we see occurring in practice exactly what one can, with a degree of imagination, visualise occurring from the diagram of FIG. 4. Whereas the free points of inflection in FIG. 5, the unstressed configuration of the expanded stent, are bravely facing each other without any circumferential staggering, as soon as the prosthesis is subject to external stresses that bend it into the banana shape evident from FIG. 6, what was previously and orderly face to face configuration of points of inflection has now become a staggered configuration, not just on the exact inside of the bend but also on the flanks of the bend that are facing the viewer in the side view of FIG. 6.

Self-evidently, the construction of FIG. 5 is hardly more complex than that of FIG. 2. Likewise, the construction of FIG. 4 is self-evidently hardly more complicated than the FIG. 3 matrix. It is one advantage of the present invention that the useful result evident in FIG. 6 can be achieved with a lattice that is barely more complicated than that of the classic lattice of WO 01/32102. That is of course not to say that the benefits of the invention are not achievable with more complicated constructions. There is now an enormous multitude of stent lattice possibilities and those who are promulgating relatively complicated lattices would doubtless assert that their specific constructions bring useful benefits. Doubtless the simple principle of the present invention can be incorporated into these more complicated arrangements, as skilled and experienced stent design readers will appreciate.

As increasing sophistication of design of stents allows them to perform in ever more demanding locations in the body, the need for stent flexibility in bending continues to increase. for maximum flexibility, one would wish for a minimum of connector portions between stenting rings. However, the point about connectors is that they do serve to keep apart from each other portions of stenting rings that might otherwise collide. There is therefore a tension between the objective of preventing collisions and the objective of greater flexibility. The present invention aims to make a contribution to this delicate contradiction, by using just a few connectors to encourage approaching points of inflection to, as it were, politely step to one side, in opposite directions, as they approach each other, rather than confronting each other head to head. Given the strength that effective stents need to exhibit, to keep bodily tissue displaced radially outwardly from the bodily lumen being stented, there should be enough strength in even just a few connectors to ease the points of inflection past each other, because only a relatively small "push" on the points of inflection, in circumferentially opposite directions, should be enough to prevent a peak-to-peak confrontation. Otherwise, when the stent in the body is not called upon to bend, then the connectors do not have to go to work to urge the facing points of inflection to move in opposite circumferential directions. The stresses in the stent matrix are those that arise anyway, when the surrounding tissue is urging the stent matrix to bend from a straight tube to a banana shape. Accordingly, the stresses within the stent matrix are in harmony with the stresses that the surrounding body tissue is experiencing, and imposing on the stent. This harmony should be of assistance in matching the performance of the metal stent matrix to the resilient properties of the surrounding bodily tissue.

There is no requirement that the skewed arrangement, that the present invention proposes, be reproduced throughout the stent lattice. For example, it may be desirable to make one portion of a stent more bend-capable than other parts. In such a case, it may be useful to confine the skewed connector distribution to those parts of the stent which are to be relatively more bend-capable. It hardly needs to be observed that the bend capability of a stent portion, before it begins to buckle, should be high enough to incur the risk of abutment of approaching points of inflection in adjacent stenting rings, to make incorporation of the skewed distribution of the invention worthwhile. Generally, the sparser the population of connector portions between the population of connector portions between stenting rings, the more bend-capability will be available.

FIG. 3 shows 6 struts between adjacent connectors in the same circle, and FIG. 4 shows 8. With 10 connectors, an unsymmetrical arrangement of the present invention suggests a heavily skewed split of 3/7 in the number of struts between each connector and the nearest one in the axially next adjacent ring of connectors (with the symmetrical arrangement being 5/5). 12 connectors seem scarcely more attractive because then the split is 4/8, still somewhat heavily skewed relative to a symmetrical 6/6 split of struts between connectors, but 14 connectors seems more attractive because that permits a 6/8 split which is close to the symmetrical 717 split of a symmetrical arrangement. One seeks an arrangement that is skewed enough to urge the approaching points of inflection on the inside of the bend to pass each other elegantly, but not such a pronounced skew that stresses in the stent lattice show pronounced differences, depending where in the lattice one is measuring them.

Generally, there will be up to 6 connectors in each circle of connectors. 3 or 4 connectors per ring are presently favoured but the number of connectors falls to be determined in harmony with many other design aspects of the stent lattice, as stent designers well know.

The radially outwardly directed force that a stent can exert against the bodily tissue forming the walls of the stented bodily lumen will inevitably be somewhat reduced, with increasing length of the gaps between axially adjacent stenting rings of the stent. Clearly then, one would choose short connectors to maximise stenting radial force. In a high flex location for the stent measures must be taken, to prevent collisions between adjacent stenting rings when the stent is subjected to serve bending. A particularly useful technical effect of the present invention is that the short connector portions allow close proximity of axially adjacent stenting rings (and so a high stenting force) yet no collisions between the closely adjacent rings when the stent suffers severe bending.

Example

To assist readers to grasp the physical dimensions of stents that are preferred embodiments of the present invention, we set out in the Table below some representative dimensions for stents studied by the Applicant. It is to be understood that these dimensions are provided not to signify precise dimensions that work better than others but merely dimensions within the ranges here contemplated.

TABLE

| | Each zig-zag ring | | | | Connector |
|---|---|---|---|---|---|
| Product | Number of struts | Struts width (µm) | Struts length (mm) | Connector length | extended length (mm)* |
| A | 24 | 160 | 1.95 | 0.8 | 1.4 |
| B | 36 | 100 | 1.45 | 0.5 | 1.0 |
| C | 30 | 100 | 1.45 | 0.5 | 1.0 |
| D | 32 | 135 | 1.55 | 0.5 | 1.0 |

*This is the full length that lies between the ends of two co-linear slits axially spaced from each other that create the two axially-facing V-points of inflection of two adjacent zig-zag rings One message to be taken from the Table is that strut lengths are going to be, in general, significantly more than 1 mm while connectors are going to exhibit a length significantly below 1 mm. The points of inflection, in themselves, typically have an axial length of 0.25 mm or 0.30 mm, which is typically around two or three times the width (in the circumferential direction) of one of the struts. Thinking of a point of inflection as a zone where the material of two struts comes together in an unslitted block of material, that block will have the width of two struts and an axial length that is similar to, or a bit longer than, such width.

In general, connectors lengths will be 0.8 mm or less, likely 0.6 mm or less. Strut lengths will likely be more than 1.25 mm, likely is a range of from 1.3 to 2.2 mm or more specifically 1.4 to 2.0 mm. One favoured construction has 32 struts per ring, such as in Product D in the Table.

For the sake of clarity, and the avoidance of doubt, the "points of inflection" referred to in this specification are not a reference to the point of inflection that each strut exhibits, mid-way along its length, which more or less inevitably appears when the slitted stent precursor tube is radially expanded from its original diameter to its working stenting diameter.

What is claimed is:

1. A stent comprising:
   a plurality of stenting rings, each stenting ring including a plurality of struts and points of inflection, each point of inflection connecting adjacent struts, the points of inflection of adjacent stenting rings facing each other along an axis parallel to a longitudinal axis of the stent in a radially expanded stenting disposition while the stent is in an unbent configuration;
   adjacent stenting rings connected by connectors extending from a point of inflection on one stenting ring to a facing point of inflection on another stenting ring, the connectors being linear along an entire length thereof and parallel to the longitudinal axis of the stent, each of the connectors having a length shorter than a length of each of the struts;
   each stenting ring including connected points of inflection and unconnected points of inflection; and
   wherein
   each of at least one pair of the connected inflection points comprises two struts and an included angle wherein the included angle of one inflection point of the pair is larger than the included angle of the other inflection point of the pair
   and
   at least two adjacent stenting rings have equal numbers of points of inflection.

2. The stent according to claim 1, wherein the struts of each stenting ring have the same cross-section, the length of each of the struts is greater than 1.25 mm, and the length of each of the connectors is less than 1 mm.

3. The stent according to claim 2, wherein at least two of the struts in a stenting ring have an equal length, such that each of the points of inflection lie in one of two circles transverse to the longitudinal axis of the stent.

4. The stent according to claim 1, wherein the number of struts "N" of a stenting ring between circumferentially adjacent connectors is such that N/2 is an even number.

5. The stent according to claim 1, wherein the number of struts "N" of a stenting ring between circumferentially adjacent connectors is such that N/2 is an odd number and N is more than 10.

6. The stent according to claim 1, wherein longitudinal-ly adjacent connectors exhibit a helical path coaxial with the longitudinal axis from a first end of the stent to a second op-posing end of the stent.

7. The stent according to claim 1, comprising a shape memory alloy.

8. The stent according to claim 1, wherein the stent undergoes plastic deformation upon expansion to the radially expanded stenting disposition.

9. The stent according to claim 1, wherein the length of each of the connectors is not more than 0.8 mm.

10. The stent according to claim 1, wherein the length of each of the connectors is less than 0.6 mm.

11. The stent according to claim 1, wherein the length of each of the struts is in a range of from 1.3 mm to 2.2 mm.

12. The stent according to claim 1, wherein the length of each of the struts is in a range of from 1.4 mm to 2.0 mm.

13. The stent according to claim 1, wherein each of the stenting rings includes 32 struts.

14. The stent according to claim 1, wherein adjacent stenting rings are connected by four evenly spaced connectors.

* * * * *